United States Patent
Lai

[11] Patent Number: 5,945,119
[45] Date of Patent: Aug. 31, 1999

[54] THERAPEUTIC PREPARATIONS CONTAINING CAESIUM IONS

[76] Inventor: John Lai, 43 Eaglehawk Road, Bendigo, Victoria 3550, Australia

[21] Appl. No.: 08/467,150

[22] Filed: Jun. 6, 1995

Related U.S. Application Data

[60] Division of application No. 08/250,566, May 27, 1994, abandoned, which is a continuation-in-part of application No. PCT/AU93/00384, Jul. 28, 1993.

[30] Foreign Application Priority Data

Jul. 31, 1992 [AU] Australia .................... PL3891

[51] Int. Cl.⁶ .................................................. A61F 13/00
[52] U.S. Cl. .......................... 424/443; 424/45; 424/46; 424/677; 424/697; 424/195.1; 424/402; 424/464; 424/451; 424/445; 424/448; 514/944; 514/947; 514/937
[58] Field of Search ................ 424/45, 46, 677, 424/697, 464, 451, 443, 445, 448, 195.1, 402; 514/944, 947, 937

[56] References Cited

U.S. PATENT DOCUMENTS

| | | | |
|---|---|---|---|
| 3,641,242 | 2/1972 | Masco | 424/443 |
| 4,728,642 | 3/1988 | Pawelchak et al. | 424/443 |
| 4,738,257 | 4/1988 | Meyes et al. | 424/443 |

FOREIGN PATENT DOCUMENTS

18756/88  1/1989  Australia .

OTHER PUBLICATIONS

Swedish Patent Abstract, SE 8604942—Cesar S.A.
Japanese Patent Abstract, J 59122421—Tokyo Iken K.K.
Japanese Patent Abstract, J 60097043—Shiseido K.K.
Japanese Patent Abstract, JP 3224690—Yasuo Yui.
A.K. Brewer, "The High pH Therapy for Cancer Test on Mice and Humans," *Pharmacology Biochemistry & Behavior*, vol. 21. Suppl. 1, pp. 1–5, 1984.
Japanese Patent Abstract, J 55069515—Meiji Seika Kaisha
Sartori, H.E., "Cesium Therapy in Cancer Patients," *Pharmacol. Biochem. Behav.*, 1984, vol. 21/Suppl., 1, pp. 11–13.

*Primary Examiner*—Raj Bawa
*Attorney, Agent, or Firm*—Christensen O'Connor Johnson & Kindness PLLC

[57] ABSTRACT

Various preparations for treating or relieving pain in a patient are disclosed wherein preparations containing caesium ions, preferably in the form of caesium chloride, and preferably also magnesium ions in the form of magnesium sulphate, are administered externally or internally to the patient. In one preferred embodiment a topical preparation is provided which consists of strips of microporous material (A) on each side of a plastics backing layer (B) impregnated with an aqueous solution containing caesium chloride and magnesium sulphate. In an alternative embodiment a cream preparation containing caesium chloride and magnesium sulphate is provided for external application to the patient.

28 Claims, 1 Drawing Sheet

THERAPEUTIC PREPARATIONS CONTAINING CAESIUM IONS

This is a divisional of the prior application Ser. No. 08/250,566, filed on May 27, 1994, now abandoned, of John Lai for THERAPEUTIC METHODS USING CAESIUM IONS, which in turn is a continuation-in-part of international application Ser. No. PCT/AU93/00384 filed on Jul. 28, 1993, John Lai, for THERAPEUTIC METHODS USING CAESIUM IONS, the benefit of the filing dates of which are hereby claimed under 35 U.S.C. §120.

This patent application is a continuing application claiming foreign priority benefits. Specifically, this patent application claims the benefit of the filing date under 35 U.S.C. §120 of International application No. PCT/AU93/00384, filed Jul. 28, 1993, and also the benefit of the filing date under 35 U.S.C. §119 of Australian patent application No. PL3891, filed Jul. 31, 1992.

FIELD OF THE INVENTION

This invention relates to the treatment of a wide variety of distressing disorders that occur in both man and animals and to compositions and preparations for use in such treatment. As used herein, the term 'patient' includes within its scope both humans and animals.

The invention finds particular application in the treatment of many seemingly unrelated complaints that cause huge health losses to individuals and huge financial losses to society. Some important applications of the present invention which have been noted to date include:

1) Relief of the pain in an extremely wide range of painful musculoskeletal and neural disorders.

2) The suppressing or relieving of any type of cough as well as most of the symptoms of hay fever. This includes such important afflictions as asthma and the common cold.

3) Relief from croup attack in children.

4) Relief from itching of the skin and related complaints such as those from eczema and other skin diseases or disorders.

5) Relief from the irritation resulting from ulcers, and also rapid healing of persistent, long-term leg ulcers.

6) Relief from local pain obtained by using subcutaneous injections.

7) Use as an anaesthetic.

The above list of therapeutic uses is not a limiting list, but simply some of the more important or more dramatic uses of this invention.

BACKGROUND OF THE INVENTION

The current conventional Western medical practice for management of arthritis and other soft tissue injuries includes the administration of steroids and non-steroidal anti-inflammatory drugs by topical application, orally or by injection into the affected areas of the patient.

Steroids, such as the corticosteroids, often have undesirable side effects such as the promotion of peptic ulcers, increased susceptibility to infection, mental irritability, nervousness, obesity, muscular weakness, osteoporosis, diabetes, and adrenal insufficiency which, in some cases, may cause the patient to collapse.

Non-steroidal anti-inflammatory drugs generally have a less debilitating effect on patients. However, they are not without side effects. Stomach disorders, gastric pain, diarrhoea, dizziness or light headiness, stomach or duodenal ulcers and long term blood loss have all been reported in patients treated with non-steroidal anti-inflammatory drugs.

Where the anti-inflammatory drugs have been administered topically, further difficulties such as skin irritation, odor and staining may also be experienced.

Most commercially available topical preparations for the treatment of musculoskeletal disorders contain methyl salicylate as the active ingredient, but methyl salicylate is a toxic drug which can be lethal in large doses and it is possible that such large lethal doses may be attained by absorption through the skin.

The administration of gold has also been promoted in the management of arthritis. However, side effects have been reported in patients receiving gold administration including toxic hepatitis, renal failure, deafness, skin rashes and various blood disorders.

It is therefore desirable to provide a method of treatment of musculoskeletal and neural disorders which alleviates or ameliorates at least some of the difficulties associated with current treatment regimes.

Traditional Chinese remedies for the treatment of soft tissue injuries such as sprains and swellings, particularly of the ankles, include the packing of raw salt extracted from seawater around a painful or swollen joint. The application of the salt reduces the pain and swelling in many cases.

Further, acupuncturists postulate that there are three dimensional ribbon-like structures called meridians which are embedded in the body and join the acupuncture points. These meridians are postulated to be present in all mammals. It is postulated further that there is a flow of energy, possibly electromagnetic energy, flowing through these meridians and if, for any reason, this flow of energy is disrupted, disease will occur. By re-establishing the energy flow, the pain and inflammation which are often associated with neural and musculoskeletal injuries or disorders, and attributable to a disruption of the flow of energy through the meridians, can be reduced and thus aid in the eventual healing process.

Japanese Patent Application JP-228513 postulates that caesium chloride, either in the form of an adhesive preparation or a paste or powder containing caesium chloride, may be applied externally to a patient to effect results similar to acupuncture or magnetic therapy in the treatment of various sprains, lumbodynia-melosalgia and dermatitis. Hitherto, however, it is believed that caesium chloride has not been used commercially in the treatment of any kind of musculoskeletal, neural, respiratory or skin disorders of a patient.

SUMMARY OF THE INVENTION

DESCRIPTION OF THE PREFERRED EMBODIMENTS

Figure 1:
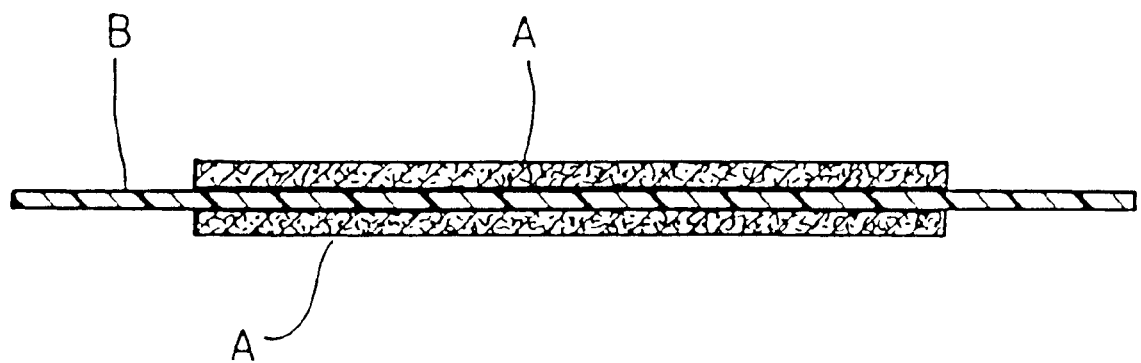
FIG. 1 illustrates a representative embodiment of the present invention, a schematic section through a plastic strip having microporous material impregnated with cesium chloride and magnesium sulphate on both sides.

The present invention in its different aspects is concerned with the external application of caesium chloride in conjunction with other compounds which produce a synergistic effect in treating a wide variety of disorders in a patient and with the use of caesium chloride, either by itself or in conjunction with other compounds, in preparations for internal administration to a patient.

According to a broad aspect of the invention there is provided a method of treating ailments and disorders of a patient wherein a preparation containing a therapeutically effective amount of caesium ions is administered internally to the patient.

According to another broad aspect of the present invention there is provided a method of treating ailments and disorders of a patient wherein a preparation containing a therapeutically effective amount of caesium ions in combination with magnesium ions is administered externally or internally to the patient.

According to a further aspect of the present invention, there is provided a method of treating musculoskeletal or neural disorders in a patient in need of such treatment, which method comprises externally administering to said patient a therapeutically effective amount of caesium ions in combination with magnesium ions. Preferably, the caesium ions are in the form of caesium chloride, CsCl, and the magnesium ions are in the form of magnesium sulphate, $MgSO_4$.

It has been found that the external application of caesium chloride reduces pain levels and swelling in swollen joints and has similar effects in the treatment of muscular disorders such as myositis.

Surprisingly, it has also been found that the addition of magnesium ions, preferably in the form of magnesium sulphate, to caesium chloride can markedly reduce the time for the pain relieving properties of the caesium chloride to take effect.

The preparation containing caesium chloride and magnesium sulphate may be applied topically in the form of a gauze or other absorbent medium which has been impregnated with an aqueous solution containing caesium chloride and magnesium sulphate. The absorbent material may comprise any gauze or tissue, such as muslin tissue or self-adhesive tissue paper, but preferably it comprises a microporous synthetic fabric material such as material sold by Minnesota Mining and Manufacturing Company under the Trade Mark "MICROPORE". The impregnated material is left to dry preferably at room temperature before being cut or otherwise severed into conveniently sized portions which may be attached to the appropriate part of the patient and secured in any convenient conventional manner.

According to another aspect of the invention there is provided a topical preparation for use in a method of treating musculoskeletal or neural disorders in a patient wherein the preparation comprises a strip or piece of absorbent material impregnated with a therapeutically effective amount of caesium chloride and magnesium sulphate.

The amount by weight of magnesium sulphate in the preparation is, preferably, at least half, but preferably does not exceed the amount by weight of caesium chloride in the preparation.

Preferably, the caesium chloride is present in the absorbent material in a quantity of between about 0.05 and about 0.5 mg per $cm^2$ of the surface area of the absorbent material, and the magnesium sulphate is present in a quantity of between about 0.025 and about 0.5 mg per $cm^2$ of the surface area of the absorbent material. Preferred amounts of caesium chloride and magnesium sulphate are between about 0.1–0.2 mg CsCl and about 0.05–0.2 mg $MgSO_4$ per $cm^2$ of the absorbent material. A preparation containing these preferred amounts of caesium chloride and magnesium sulphate may be obtained by immersing 360 m of a microporous strip 10 cm wide in one liter of an aqueous solution containing 36–72 g/l of caesium chloride and 18–72 g/l of magnesium sulphate, and then drying the microporous strip.

A preferred embodiment of this aspect of the invention will now be described with reference to the following example and to the accompanying drawing, FIG. 1, which is a schematic section through a plastic strip having microporous material impregnated with caesium chloride and magnesium sulphate on both sides.

EXAMPLE 1

(1) One strip (A) of a self-adhesive microporous fabric material such as "Micropore" 10 cm wide is applied on each side of a layer of plastic (B), hence the plastic layer (B) is sandwiched between the two layers (A) of the microporous material.

(2) The strip-like product is then immersed in one liter of an aqueous solution containing 60 g/l of caesium chloride and 30–60 g/l of magnesium sulphate for about 12 hours, after which it is taken out of the solution and dried.

(3) The strip-like product can then be cut into patches of different sizes and the layers (A) of impregnated microporous material peeled off either side of the plastic strip (B) as required for application onto the skin of a patient. Amount of Caesium Chloride and Magnesium Sulphate in Patches of the Strip 60 g of CsCl and 30–60 g of $MgSO_4$ in 1 liter of water, can produce 360 meters of the strip. If 30 g of $MgSO_4$ is used, the amounts of CsCl and $MgSO_4$ per meter of the strip are as follows:

60 g/360 m=0.166 g/m CsCl and 30 g/360 m=0.083 g/m $MgSO_4$.

The strip is 10 cm wide and so the area of 1 meter of the strip is 1000 $cm^2$.

Thus each $cm^2$ of the strip contains 0.166 mg of caesium chloride, and 0.083 mg of magnesium sulphate.

Experiments have indicated that it takes at least one hour to achieve a decrease in pain levels in test patients following the application of a microporous strip impregnated with caesium chloride per se, whereas the addition of magnesium ions, preferably in the form of magnesium sulphate, to the solution with which the strip is impregnated has, surprisingly, been found to shorten the effective time for pain relief to occur from hours to minutes. Most patients have found that a microporous strip impregnated with caesium chloride and magnesium sulphate provides pain relief within 10 to 30 minutes.

Tests have indicated further that a microporous strip impregnated with caesium chloride and magnesium sulphate can remain effective for a considerable period of time of possibly up to six months or even longer, regardless of where the impregnated microporous strip is stored. This may be due to the fact that caesium chloride is a very stable compound and it is only slightly hygroscopic and remains substantially dry in the air. Further, the impregnated strip will not melt in the heat or go hard in cold conditions; it does not become lumpy when wet; and it does not become uncomfortable to the patient if left on the body for days. Also, the microporous nature of the strip allows the body to breath through the strip, allowing the strip to be left on the skin for up to two weeks; and the strip is thin enough to allow the patient to put on stockings, socks and shoes without much discomfort, whereas the strip is strong enough to be used as a bandage to stabilize a sprain or fracture.

Increased concentrations of caesium chloride alone have not been shown to have any significant effect in reducing pain and swelling levels, nor any significant decrease in time in achieving the reduced pain and swelling levels when compared with tissues or strip impregnated with the aqueous solution of caesium chloride and magnesium sulphate as above.

Conversely, concentrations as low as 0.1 g CsCl per liter of water have been shown to be effective although the time taken to achieve the desired reduction in pain and swelling levels is greatly increased. In the case of muslin tissue impregnated solely with 1 g CsCl/per liter of water, it may take at least three to four days before a patient observes any significant effect in the reduction of swelling and pain levels.

It will, however, be appreciated that the method of the present invention may be performed using different forms of preparations containing caesium chloride and magnesium sulphate for external application to a patient. For instance, the method of the present invention in its broadest ambit includes the external application to a patient of therapeutically effective amounts of caesium chloride and magnesium ions contained in creams, pastes, lotions and sprays or the like, and even bath salts containing caesium chloride and magnesium ions which may be added to baths, spa baths, mud baths etc. to provide a therapeutically effective amount of caesium chloride and magnesium ions in the bath. It is also contemplated that, within the scope of the present invention, herbs or plants may be grown in caesium and magnesium enriched or fertilized soils or hydroponic solutions, with the plants being used to make preparations to be applied externally to a patient. Similarly, caesium enriched clays containing therapeutically effective amounts of caesium chloride may be applied externally to a patient.

There is also provided, in accordance with a further aspect of the invention a topical preparation for external application to a patient wherein the preparation comprises a cream containing a therapeutically effective amount of caesium ions and magnesium ions, preferably in the forms of caesium chloride and magnesium sulphate.

The caesium chloride and magnesium sulphate may be incorporated into a cream base by conventional means known in the art. Preferably, the caesium chloride is present in the cream in a quantity of between about 0.1% and about 5% of the total weight of the preparation, and the magnesium sulphate is present in a quantity of between about 0.025% and about 5% of the total weight of the preparation. The amount by weight of magnesium sulphate is preferably at least half, but preferably does not exceed the amount by weight of caesium chloride in the preparation. Convenient concentrations of caesium chloride have been shown to be of the order of about 5 to about 30 g/kg of cream base, preferably about 10 g/kg, and convenient concentrations of magnesium sulphate are between about 2.5 to about 30 g/kg, preferably between about 5–10 g/kg.

A preferred embodiment of this aspect of the present invention will now be described in the following example.

EXAMPLE 2

100 g of caesium chloride and 50–100 g of magnesium sulphate is mixed with 10 kg of an aqueous cream base, then bottled in 50 ml jars.

Content of Caesium Chloride and Magnesium Sulphate in the Cream 100 g CsCl and 50–100 g $MgSO_4$ in 10 kg of cream=10 g CsCl and 5–10 g $MgSO_4$ in 1 kg of cream=10 mg of CsCl and 5–10 mg of $MgSO_4$ in 1 g of cream=500 mg CsCl and 250–500 mg $MgSO_4$ in 50 g of cream (1 jar).

The cream may be applied by massaging gently into the affected areas and has been shown to provide positive effects approximately one hour after application and to provide relief for up to 6 hours.

The cream containing caesium chloride and magnesium sulphate is very safe. Ingestion of 100 g of the cream (1 g CsCl and 0.5–1.0 g $MgSO_4$) will not cause any ill effect in the patient. It has no colours, no smell and does not cause irritation to the skin. Further, it does not cause irritation to the eyes, and is easily washed off with water.

Whilst treatment with cream containing caesium chloride alone will provide relief from arthritic pain within an hour or so, the addition of magnesium sulphate to the cream decreases the time for the cream to take effect to between 10 and 30 minutes. Cream in accordance with the invention containing both caesium chloride and magnesium sulphate therefore provides virtually immediate relief from pain, and indeed, the long term application has been shown, in some trial patients, to bring about total remission of arthritic pain. Preparations containing caesium chloride and magnesium sulphate is have also been shown to provide beneficial effects when used in conjunction with orthodox methods of treatment, for example, physiotherapy or acupuncture.

For example, a badly sprained ankle treated by orthodox medical techniques, that is, physiotherapy, will take approximately two weeks to heal sufficiently for the patient to walk without significant discomfort. With acupuncture or laser acupuncture, the healing time may be decreased to approximately one week.

If the ankle were treated with caesium chloride alone, a similar healing time, that is, up to one week, would be observed. However, if a preparation containing caesium chloride and magnesium sulphate is employed in conjunction with, say, acupuncture or laser acupuncture, healing will be effected in approximately three to four days only.

Apart from the treatment of musculoskeletal disorders including rheumatic or arthritic disorders, the external application of preparations containing caesium ions and magnesium ions to patients having painful varicose veins, and neural disorders such as, migraines or other severe headaches, toothache, period pains and stomach pains, has been demonstrated to provide significant relief in pain levels experienced by the patient.

A further beneficial application of preparations containing caesium ions, preferably caesium chloride, whether alone or in conjunction with magnesium ions, is the application of the preparation internally or externally to relieve coughing in a patient suffering from a respiratory disorder.

Thus, according to another broad aspect of the invention there is provided a method of treating disorders of the respiratory system of a patient, which method comprises administering to said patient a therapeutically effective amount of a preparation containing caesium ions, preferably caesium chloride.

This method of treatment finds particular application in the relief of coughing and chest congestion, the relief from croup attack in children, as well as relief of the symptoms of hayfever. It will, however, be appreciated that the invention is not limited thereto and the treatment of patients having other symptoms of respiratory disorders such as blocked or runny noses or other symptoms of asthma, common colds and influenza falls within the ambit of the present invention.

In treating respiratory disorders the caesium ions may be administered either externally or internally to the patient.

The caesium ions are preferably administered externally by applying a topical preparation, for instance a cream, containing caesium chloride, and preferably also magnesium ions, to the chest, throat, nasal area or other part of the body of the patient. The present invention therefore includes within its ambit a topical preparation for use in the treatment of respiratory disorders, wherein the preparation contains a therapeutically effective amount of caesium ions and magnesium ions, preferably in the forms of caesium chloride and magnesium sulphate.

The preparation is preferably applied topically in the form of a cream containing caesium chloride and magnesium sulphate.

The caesium chloride and magnesium sulphate may be incorporated into a cream base by conventional means known in the art. The cream preparation described above for use in the treatment of musculoskeletal and neural disorders has been found to be equally effective in relieving coughing and chest congestion in patients suffering from respiratory disorders. As described above, the caesium chloride is preferably present in the cream in a quantity of between about 0.1% and about 5% of the total weight of the preparation, and the magnesium sulphate is preferably present in a quantity of between about 0.05% and about 5% of the total weight of the preparation. The amount by weight of magnesium sulphate is preferably at least half, but preferably does not exceed the amount by weight of caesium chloride in the preparation. Convenient concentrations of caesium chloride have been shown to be of the order of about 2.5 to about 30 g/kg of cream base, preferably about 10 g/kg (1% CsCl), and convenient concentrations of magnesium sulphate are between about 2.5 to about 30 g/kg, preferably between about 5–10 g/kg (0.5–1% $MgSO_4$).

Recommended therapeutic amounts of caesium chloride and magnesium sulphate for external application to a patient are between about 0.005 mg and about 0.05 mg CsCl, preferably between about 0.010 mg and about 0.020 mg of caesium chloride, and between about 0.0025 mg and about 0.05 mg $MgSO_4$, preferably between about 0.005 and about 0.020 mg of magnesium sulphate, per $cm^2$ of the skin of the patient. These preferred amounts of caesium chloride and magnesium sulphate may be provided by applying 10 mg of cream containing about 1% caesium chloride and about 0.5–1% magnesium sulphate over an area of skin of 9 $cm^2$ thereby administering approximately 0.0111 mg of CsCl and 0.0055–0.0011 mg of $MgSO_4$ per $cm^2$ of skin.

A preferred embodiment of this aspect of the present invention will now be described in the following example.

EXAMPLE 3

100 g of caesium chloride and 50–100 g magnesium sulphate is mixed with 10 kg of an aqueous cream base, then bottled in 50 ml jars.

Content of Caesium Chloride and Magnesium Sulphate in the Cream

- 100 g CsCl and 50–100 g $MgSO_4$ in 10 kg of cream=10 g CsCl and 5–10 g $MgSO_4$ in 1 kg of cream=10 mg of CsCl and 5–10 mg $MgSO_4$ in 1 g of cream
- One gram of cream can cover 900 $cm^2$ of skin 10 mg CsCl/900 $cm^2$=0.0111 mg CsCl/$cm^2$ and 5 mg $MgSO_4$/900 $cm^2$=0.0055 mg $MgSO_4$/$cm^2$ The cream may be applied by massaging gently into the affected area, such as the chest or throat and has been shown to provide positive suppression of coughing within a few minutes after application. The cream can also provide relief of most symptoms of hayfever by applying it around the nasal area.

Surprisingly, it has also been found that caesium ions, preferably in the form of caesium chloride, with or without magnesium ions, administered internally to a patient also have beneficial effects in suppressing or relieving any type of cough, as well as relieving most symptoms of hayfever. The caesium ions may be administered internally in any convenient form, for instance, an aqueous solution of caesium chloride could be used in a nebulizer, in an aerosol inhaler, in a nasal spray, as a mouth wash or administered with a dropper. Additionally, caesium chloride could be added to a liquid or syrup to produce a cough mixture. Thus, the present invention also includes within its ambit a preparation for internal administration to a patient for treating coughs, respiratory disorders or hayfever, wherein the preparation includes a therapeutically effective amount of caesium ions.

In a preferred embodiment of this aspect of the invention the preparation comprises an aqueous solution of caesium chloride containing between about 0.5% and about 4% of caesium chloride. Such a solution is preferably placed within a nebulizer or aerosol inhaler for administration to a patient who preferably inhales a dose of between about 0.2 mg and about 1.6 mg of caesium chloride from the nebulizer or aerosol inhaler as described with reference to the following example.

EXAMPLE 4

An amount of caesium chloride (CsCl) is dissolved in distilled water to produce a solution containing about 1% caesium chloride, 2 ml of which is then placed in a nebulizer or aerosol inhaler.

2 ml of a 1% solution contains 0.02 g CsCl. 2 ml of 1% CsCl solution is a sufficient quantity of solution for 50 inhalations or "puffs". Thus, each puff or inhalation from the nebulizer contains 0.4 mg of CsCl.

Inhalations containing between 0.2 mg and 0.4 mg caesium chloride have been found to suppress coughs within a matter of a few minutes, and such inhalations have also been found to suppress and relieve symptoms of hayfever. No significantly adverse effects have been noticed in patients that have repeatedly inhaled doses of caesium chloride from a nebulizer or aerosol inhaler. The only side effect noticed in a patient taking twenty inhalations in close succession from a nebulizer containing a 1% solution of caesium chloride has been a slight numb feeling on the tongue of the patient.

Caesium chloride appears to be a selective blocker for local nerve endings. In this case, it blocks the transmission of a signal that would result in a cough. It also has an anti-histamine like property, since it can suppress the symptoms of hayfever, although the actual mechanism is not clear. It also has a bronchodilatory effect, which is more powerful than the most commonly used bronchial dilator SALBUTAMOL(VENTOLIN).

At present, all expectorants, antitussives and decongestants are mixtures of antihistamines, such as tripolidine, pheniramine, diphenhydramine and dexchlorpheniramine with or without pseudoephedrine, (a central nervous system stimulant), or codeine phosphate or pholcodine which act to depress the Central Nervous System (CNS). Even at therapeutic doses, most of the treatments commonly in use cause some degree of drowsiness, sedation, nausea, dizziness, weakness, anxiety or insomnia. Pseudoephedrine and phenylephrine can cause high blood pressure, and are therefore dangerous for people already suffering from high blood pressure.

Pseudoephedrine can cause death at a level of only six times the therapeutic dose.

A 75 kg person ingested 4 g of caesium chloride on an empty stomach with no adverse effects. This same person on earlier separate occasions ingested 1, 2 or 3 grams of caesium chloride in 50 ml of water into an empty stomach with no adverse effects. Five grams of caesium chloride in 50 ml of water is too bitter to drink. Animal experimentation has shown that intravenous injections of 3.4 g of caesium chloride will not cause arrhythmia in a 20 kg dog.

Caesium chloride is a far safer and more effective antitussive and decongestant than any one of the above. It may actually be as safe as NaCl.

An asthma attack in a chronic sufferer has been stopped in a few minutes. Such attacks are capable of being fatal if they continue, therefore interrupting the fatal feed-back loop is of vital importance. Four puffs of a 4% solution of caesium chloride from a nebulizer, enabled a singer, with chronic asthma, to sing for 3 hours without stopping. This person was unable to obtain enough relief from other products on the market to be able to pursue their singing career.

Coughs due to colds cause extreme distress to typical northern hemisphere wintertime residents. Any treatment that would reduce the drain of energy and health in the course of the cold would certainly help in recovery from the common cold.

Croup attack in children can be a terrifying experience to a child too young to be able to understand the explanations made by adults. The incessant nature of this complaint can easily cause more pain and suffering to the parents than to the child. However, cream containing caesium chloride and magnesium sulphate rapidly brings relief to both the child and indirectly to the parents.

A cream preparation containing caesium chloride and magnesium sulphate as described above was applied to the throat of a child that regularly loses sleep (along with the concerned parents) when having croup problems.

A placebo cream, the caesium chloride and magnesium sulphate cream, and a traditional cough mixture were used alternatively and in all possible combinations. The parents tried every possibility to demonstrate that the child was reacting to mental and physical placebo effects.

Following more than three weeks of trials the parents became convinced that it was the cream containing caesium chloride and magnesium sulphate that stopped the croup symptoms and allowed both the child and the parents to sleep at night.

It is desirable to state that many different kinds of cough can be suppressed because it is postulated that the caesium chloride is selectively blocking the nerves rather than responding to a specific affliction that produces that cough. Here the intrinsic healing capabilities of the body are potentiated by removal of the antagonism caused by coughing.

It has also been found that preparations containing caesium ions and magnesium ions may also be applied externally to a patient to provide relief from itching and to promote the healing of a wide variety of skin complaints and disorders, and in accordance with a further aspect of the present invention there is provided a method of treating skin disorders in a patient, which method comprises administering to said patient a therapeutically effective amount of a preparation containing caesium ions and magnesium ions, preferably in the forms of caesium chloride and magnesium sulphate respectively.

The term skin disorders will be understood to include eczema and a wide variety of other skin complaints, including rashes, body sores and ulcers. This method of the invention is particularly effective in providing relief from itching associated with such skin complaints.

To provide relief from itching, caesium ions and magnesium ions are preferably administered externally to the patient by applying a topical preparation containing caesium chloride and magnesium sulphate to the affected area. The present invention thus includes within its ambit a topical preparation for use in the treatment of skin disorders, wherein the preparation contains a therapeutically effective amount of caesium ions and magnesium ions, preferably in the form of caesium chloride and magnesium sulphate.

The preparation is preferably applied topically in the form of a cream containing caesium chloride and magnesium sulphate. In particular, creams containing the concentrations described above with reference to the treatment of musculoskeletal and neural disorders and respiratory disorders have been found to be effective in providing relief from itching by applying the cream containing caesium chloride and magnesium sulphate to the skin on or near the affected area.

In one case, eczema, which was present for three years and not responsive to a whole series of commonly available methods of treatment, was quickly cured. Within three days of starting to use the cream containing caesium chloride and magnesium sulphate the eczema nearly disappeared. The ugly sores from scratching the legs and buttocks quickly disappeared too.

If the itching sensation is relieved, the need to scratch disappears and the body uses its intrinsic capabilities to repair the damaged areas. Thus the treatment of eczema was solved in an indirect but highly desirable way.

The use of the caesium and magnesium based cream should therefore bring improvements to many itching related skin problems where the body can recover, unaided, if the scratching ceases.

The potential to help the body heal itself seems to extend beyond simply breaking the negative feed-back loop of scratching, leading to scratch-producing damage, resulting in further spread of the problem and the increased problem leading to greater scratching tendencies.

Poison ivy rash can be overcome by pure determination not to scratch. Removing the desire to scratch the rash caused by poison ivy (or other stimulants) certainly could help solve the problem for less determined victims of this affliction.

Relief from the irritation of some leg ulcers has been achieved by applying to the ulcers a preparation containing caesium chloride and magnesium sulphate, and in particular a strip or patch of absorbent material impregnated with a therapeutically effective amount of caesium chloride and magnesium sulphate such as is described in Example 1 above.

In one example a leg ulcer was covered with a patch of absorbent fabric containing about 0.5 mg of caesium chloride and about 0.25–0.5 mg of magnesium sulphate per $cm^2$ of the fabric and the patch was changed daily. This open leg ulcer had been treated in various ways by numerous medical experts over a period of two years but no improvement had been made. The ulcer measured 50 mm×75 mm before treatment started.

In one week of patch applications, the ulcer shrunk to ⅓ of its original size. The new, healthy skin virtually grew under the observer's eyes.

In the second leg ulcer example, a deep chronic ulcer refused to improve in spite of conscientious adherence to normal, accepted treatment methods. In three days this 15 mm diameter ulcer had completely healed following application of a patch of absorbent fabric containing caesium chloride and magnesium sulphate as described in the first example.

According to yet another aspect of the invention there is provided a method of anaesthetizing a person or animal wherein a preparation containing caesium ions, preferably caesium chloride, with or without magnesium ions, is administered to the person or animal to act as a local anaesthetic. The caesium ions are preferably administered to a patient in the form of an aqueous solution of caesium chloride which may be injected subcutaneously into the patient. Thus the present invention also includes within its broad ambit an anaesthetic preparation comprising a solution containing a sufficient amount of caesium ions, preferably in the form of caesium chloride, to act as an anaesthetic. The anaesthetic preparation may also include magnesium ions, preferably in the form of magnesium sulphate. Preferably, the aqueous solution contains from about 0.5% to about 4% of caesium chloride.

One advantage of using caesium chloride solution as a local anaesthetic is that it does not have a euphoric side effect nor does it remove the touch sensation. Everyone is familiar with the local anaesthetic effects on the jaw and face after a visit to the dentist.

Caesium chloride does not affect the touch sensation but only removes the pain sensations. So dental use would not cause the patient to have the disturbing loss of touch feelings that have long been normally associated with visits to the dentist.

To demonstrate the anaesthetic nature of caesium ions the following experiment was performed:
Materials
1) 3 ml of distilled water
2) 1 ml of about 2% caesium chloride solution.
Trial
1) One ml of distilled water was injected into a marked area on the left arm. The injection induced severe pain shooting up and down the left arm. The pain was so severe, it almost paralyzed the whole arm and gradually subsided within 3 minutes.
2) One ml of about 2% caesium chloride was injected into a marked area on the right arm. The injection caused some burning pain but not severe pain. It lasted about 30 seconds.
3) One ml of distilled water was then injected into the marked area on the right arm which had been primed with caesium chloride. Only slight burning pain was experienced.
4) One ml of distilled water was injected into the marked area on the left arm 5 minutes after the first injection. The second injection induced the same severe pain as the first one.
Results
1) No damage to body tissue resulted. The marked areas were free of redness and swelling. The result is that neither the distilled water nor the caesium chloride solution did damage to the body tissue.
2) Fast pain relief was achieved without interference with nerve endings or sensations other than pain sensations. The area did not develop a numbed touch sensation as other local anaesthetic do and the injection of distilled water after the caesium chloride solution injection did not elicit any pain.
3) No systemic reaction was produced following the subcutaneous injection of 20 mg of caesium chloride in solution.
4) Of course, it is normal, and it was expected that the distilled water injection would cause severe pain in the whole arm and a near paralyzed feeling that would last for 3 minutes.

From the above description, it will be appreciated that the various methods of therapeutic and anaesthetic treatment of the present invention may be regarded as two different, but related aspects. First, the effect of caesium chloride in relieving pain, suppressing coughs and treating skin disorders (first identified in JP-228513) can be markedly accelerated by the addition of magnesium ions, and it is believed in some cases the addition of magnesium ions to caesium chloride can produce a pain relieving effect where preparations comprising caesium chloride alone have failed. Secondly, the present invention has identified that preparations including caesium ions, preferably caesium chloride, either alone or in combination with magnesium ions, can be administered internally for various therapeutic treatments, particularly for treating respiratory and bronchial disorders, and also as a local anaesthetic.

I claim:

1. A pharmaceutical preparation consisting of caesium ions and magnesium ions, as therapeutically active ingredients, and a carrier for topical administration to a patient wherein the preparation comprises an absorbent material impregnated with caesium ions and magnesium ions.

2. A pharmaceutical preparation consisting of caesium ions and magnesium ions, as therapeutically active ingredients, and a carrier for topical administration to a patient wherein the preparation comprises a cream, paste, lotion, or spray containing caesium ions and magnesium ions.

3. A preparation according to claim 1 wherein the caesium ions are present in the form of caesium chloride.

4. A preparation according to claim 1 wherein the magnesium ions are present in the form of magnesium sulphate.

5. A preparation according to claim 1 wherein the absorbent material contains caesium chloride in a quantity from about 0.05 to about 0.5 mg/cm$^2$ of the surface area of the absorbent material.

6. A preparation according to claim 1 wherein the absorbent material contains magnesium sulphate in a quantity from about 0.025 to about 0.5 mg/cm$^2$ of the surface area of the absorbent material.

7. A preparation according to claim 1 wherein the absorbent material contains caesium chloride in a quantity from about 0.1 to about 0.2 mg/cm$^2$ of the surface area of the absorbent material, and magnesium sulphate in a quantity from about 0.05 to about 0.2 mg/cm$^2$ of the absorbent material.

8. A preparation according to claim 1 wherein the absorbent material is impregnated with an aqueous solution containing caesium chloride and magnesium sulphate.

9. A preparation according to claim 8 wherein the absorbent material is impregnated with an aqueous solution containing a concentration of caesium chloride from about 36 g/L to about 72 g/L, and a concentration of magnesium sulphate from about 18 g/L to about 72 g/L.

10. A preparation according to claim 1 wherein the absorbent material has a backing layer of plastics material.

11. A preparation according to claim 1 comprising a pair of absorbent materials impregnated with caesium ions and magnesium ions and a layer of plastics backing material sandwiched therebetween.

12. A preparation according to claim 1 wherein the absorbent material is selected from the group consisting of a gauze, muslin tissue, self-adhesive tissue paper, and a microporous synthetic fabric material.

13. A preparation according to claim 2 wherein the preparation contains caesium chloride present in a quantity from about 0.1% to about 5% of the total weight of the preparation.

14. A preparation according to claim 13 wherein the preparation contains magnesium sulphate present in a quantity from about 0.05% to about 5% of the total weight of the preparation.

15. A preparation according to claim 2 wherein the preparation is in the form of a cream comprising a cream base and quantities of caesium chloride and magnesium sulphate mixed into the cream base.

16. A preparation according to claim 15 wherein the caesium chloride is present in the cream in a quantity from about 5 to about 30 g/kg of the cream base.

17. A preparation according to claim 15 wherein the magnesium sulphate is present in the cream in a quantity from about 2.5 to about 30 g/kg of the cream base.

18. A preparation according to claim 17 wherein the caesium chloride is present in the cream base in a quantity of about 10 g/kg of the cream base and the magnesium sulphate is present in a quantity from about 5 to about 10 g/kg of the cream base.

19. A preparation according to claim 4 wherein the amount of magnesium sulphate by weight in the preparation is at least half the amount by weight of caesium chloride.

20. A preparation according to claim 4 wherein the amount of magnesium sulphate by weight in the preparation does not exceed the amount of caesium chloride by weight in the preparation.

21. A pharmaceutical preparation consisting of caesium ions and magnesium ions, as therapeutically active ingredients, and a carrier for internal administration to a patient wherein the preparation comprises a solution of caesium ions and magnesium ions.

22. A preparation according to claim 21 wherein the caesium ions are present in the form of caesium chloride.

23. A preparation according to claim 21 wherein the magnesium ions are present in the form of magnesium sulphate.

24. A preparation according to claim 21 wherein the solution is an aqueous solution of caesium chloride and magnesium sulphate.

25. A preparation according to claim 24 wherein the aqueous solution contains from about 0.5% to about 4% of caesium chloride.

26. A preparation according to claim 25 wherein the aqueous solution contains about 2% of caesium chloride.

27. A preparation according to claim 2 wherein the caesium ions are present in the form of caesium chloride.

28. A preparation according to claim 2 wherein the magnesium ions are present in the form of magnesium sulphate.

* * * * *

UNITED STATES PATENT AND TRADEMARK OFFICE
CERTIFICATE OF CORRECTION

PATENT NO. : 5,945,119
DATED : August 31, 1999
INVENTOR(S) : J. Lai

It is certified that error appears in the above-identified patent and that said Letters Patent is hereby corrected as shown below:

On the title page: Item
[56] Refs. Cited (U.S. Patents, Item 3) Pg. 1, Col. 1    "Meyes et al." should read --Meyer et al.--

[57]    1 – 12

Abstract

A pharmaceutical preparation containing caesium and magnesium ions as therapeutically active ingredients. For topical administration, the preparation is impregnated in an absorbent material, or contained in a cream, paste, lotion, or spray. For internal administration, the preparation is a solution.

UNITED STATES PATENT AND TRADEMARK OFFICE
CERTIFICATE OF CORRECTION

PATENT NO. : 5,945,119
DATED : August 31, 1999
INVENTOR(S) : J. Lai

It is certified that error appears in the above-identified patent and that said Letters Patent is hereby corrected as shown below:

| COLUMN | LINE | |
|---|---|---|
| 1 | 4 – 18 | Cross-Reference to Related Applications<br><br>This application is a divisional of U.S. patent application Serial No. 08/250,566, filed May 27, 1994, now abandoned, which is a continuation-in-part of PCT/AU93/00384, the benefit of the priority of the filing dates of which is hereby claimed under 35 U.S.C. § 120; the benefit of the priority of the filing date of Australian patent application No. PL3891, filed July 31, 1991, now abandoned, a continuing application of which is now Australian Patent No. 674151, is claimed under 35 U.S.C. § 119. |
| 12 | 13 – 18<br>Claim 1 | 1. A pharmaceutical preparation consisting of caesium ions and magnesium ions, as therapeutically active ingredients, and a carrier for topical administration to a patient the absorbent material being impregnated with caesium ions and magnesium ions. |
| 12 | 19 – 24<br>Claim 2 | 2. A pharmaceutical preparation consisting of caesium ions and magnesium ions, as therapeutically active ingredients, and a carrier for topical administration to a patient, the preparation being a cream, paste, lotion, or spray. |

UNITED STATES PATENT AND TRADEMARK OFFICE
CERTIFICATE OF CORRECTION

PATENT NO. : 5,945,119
DATED : August 31, 1999
INVENTOR(S) : J. Lai

It is certified that error appears in the above-indentified patent and that said Letters Patent is hereby corrected as shown below:

| COLUMN | LINE | |
|---|---|---|
| 12 | 43 – 45<br>Claim 8 | 8. A preparation according to Claim 80 wherein the absorbent material is impregnated with caesium chloride and magnesium sulphate. |
| 13 | 1 – 4<br>Claim 15 | 15. A preparation according to Claim 81 wherein the preparation is a cream having a cream base and caesium chloride and magnesium sulphate mixed into the cream base. |
| 13 to 14 | 23 to 3<br>Claim 21 | 21. A pharmaceutical preparation consisting of caesium ions and magnesium ions, as therapeutically active ingredients, and a carrier for internal administration to a patient, the preparation being a solution. |

Signed and Sealed this

Ninth Day of January, 2001

Attest:

Q. TODD DICKINSON

*Attesting Officer*          *Commissioner of Patents and Trademarks*

UNITED STATES PATENT AND TRADEMARK OFFICE
CERTIFICATE OF CORRECTION

PATENT NO. : 5,945,119
DATED : August 31, 1999
INVENTOR(S) : Lai

It is certified that error appears in the above-identified patent and that said Letters Patent is hereby corrected as shown below:

Claim 1, should read as follows:

1. A pharmaceutical preparation consisting of caesium ions and magnesium ions, as therapeutically active ingredients, and a carrier for topical administration to a patient, the <u>preparation being an</u> absorbent material [being] impregnated with caesium ions and magnesium ions.

Signed and Sealed this

Second Day of October, 2001

Attest:

*Nicholas P. Godici*

NICHOLAS P. GODICI
*Attesting Officer*     *Acting Director of the United States Patent and Trademark Office*

UNITED STATES PATENT AND TRADEMARK OFFICE
CERTIFICATE OF CORRECTION

PATENT NO. : 5,945,119
DATED : August 31, 1999
INVENTOR(S) : Lai

It is certified that error appears in the above-identified patent and that said Letters Patent is hereby corrected as shown below:

Claim 1, should read as follows:

1. A pharmaceutical preparation consisting of caesium ions and magnesium ions, as therapeutically active ingredients, and a carrier for topical administration to a patient, the preparation being an absorbent material [being] impregnated with caesium ions and magnesium ions.

Signed and Sealed this

Fourth Day of December, 2001

Attest:

NICHOLAS P. GODICI
Attesting Officer        Acting Director of the United States Patent and Trademark Office

UNITED STATES PATENT AND TRADEMARK OFFICE
CERTIFICATE OF CORRECTION

PATENT NO.   : 5,945,119
DATED        : August 31, 1999
INVENTOR(S)  : J. Lai

It is certified that error appears in the above-identified patent and that said Letters Patent is hereby corrected as shown below:

Title page,
Item [56], References Cited, U.S. PATENT DOCUMENTS,
Line 3, should read "Meyes et al." -- Meyer et al. --.

Item [57], lines 1-12,
ABSTRACT
-- A pharmaceutical preparation containing caesium and magnesium ions as therapeutically active ingredients. For topical administration, the preparation is impregnated in an absorbent material, or contained in a cream, paste, lotion, or spray. For internal administration, the preparation is a solution. --

Column 1,
Lines 4-18, insert the following:

Cross-Reference to Related Applications
-- This application is a divisional of U.S. patent application Serial No. 08/250,566, filed May 27, 1994, Now abandoned, which is a continuation-in-part of PCT/AU93/00384, the benefit of the priority of the filing dates of which is hereby claimed under 35 U.S.C. § 120; the benefit of the priority of the filing date of Australian patent application No. PL3891, filed July 31, 1991, now abandoned, a continuing application of which is now Australian Patent No. 674151, is claimed under 35 U.S.C. § 119.

UNITED STATES PATENT AND TRADEMARK OFFICE
CERTIFICATE OF CORRECTION

PATENT NO. : 5,945,119
DATED : August 31, 1999
INVENTOR(S) : J. Lai

It is certified that error appears in the above-identified patent and that said Letters Patent is hereby corrected as shown below:

Column 12,
Line 13-18, insert the following:

1. A pharmaceutical preparation consisting of caesium ions and magnesium ions, as therapeutically active ingredients, and a carrier for topical administration wich caesium ions and magnesium ions.

Line 19-24,

2. A pharmaceutical preparation consisting of caesium ions and magnesium ions, as therapeutically active ingredients, and a carrier for topical administration to a patient, the preparation being a cream, paste, lotion, or spray.

Line 43-45,

8. A preparation according to Claim 1 wherein the absorbent material is impregnated with caesium chloride and magnesium sulphate.

Column 13,
Line 1-4, insert the following:

15. A preparation according to Claim 2 wherein the preparation is a cream having a cream base and caesium chloride and magnesium sulphate mixed into the cream base.

UNITED STATES PATENT AND TRADEMARK OFFICE
CERTIFICATE OF CORRECTION

PATENT NO.   : 5,945,119
DATED        : August 31, 1999
INVENTOR(S)  : J. Lai

It is certified that error appears in the above-identified patent and that said Letters Patent is hereby corrected as shown below:

<u>Column 13 to 14, claim 21,</u>
Line 23 to 3, insert the following:

21. A pharmaceutical preparation consisting of caesium ions and magnesium ions, as therapeutically active ingredients, and a carrier for internal administration to a patient, the preparation being a solution.

This certificate supersedes Certificate of Correction issued January 9, 2001.

Signed and Sealed this

Fifth Day of February, 2002

Attest:

JAMES E. ROGAN
*Attesting Officer*   *Director of the United States Patent and Trademark Office*

UNITED STATES PATENT AND TRADEMARK OFFICE
CERTIFICATE OF CORRECTION

PATENT NO. : 5,945,119
DATED : August 31, 1999
INVENTOR(S) : J. Lai

It is certified that error appears in the above-identified patent and that said Letters Patent is hereby corrected as shown below:

Title page,
Item [56], References Cited, U.S. PATENT DOCUMENTS,
Line 3, "Meyes et al." should read -- Meyer et al. --.

Item [57], lines 1-12,
ABSTRACT
-- A pharmaceutical preparation containing caesium and
magnesium ions as therapeutically active ingredients.
For topical administration, the preparation is
impregnated in an absorbent material, or contained in
a cream, paste, lotion, or spray. For internal admin-
istration, the preparation is a solution. --

Column 1,
Lines 4-18, insert the following:

Cross-Reference to Related Applications
-- This application is a divisional of U.S. patent
application Serial No. 08/250,566, filed May 27, 1994,
Now abandoned, which is a continuation-in-part of
PCT/AU93/00384, the benefit of the priority of the
filing dates of which is hereby claimed under 35 U.S.C.
§ 120; the benefit of the priority of the filing date of
Australian patent application No. PL3891, filed
July 31, 1991, now abandoned, a continuine appli-
cation of which is now Australian Patent No. 674151,
is claimed under 35 U.S.C. § 119.

UNITED STATES PATENT AND TRADEMARK OFFICE
CERTIFICATE OF CORRECTION

PATENT NO. : 5,945,119
DATED : August 31, 1999
INVENTOR(S) : J. Lai

It is certified that error appears in the above-identified patent and that said Letters Patent is hereby corrected as shown below:

Column 12,
Lines 13-18, insert the following:

1. A pharmaceutical preparation consisting of caesium ions and magnesium ions, as therapeutically active ingredients, and a carrier for topical administration to a patient the absorbent material being impregnated with caesium ions and magnesium ions.

Lines 19-24,

2. A pharmaceutical preparation consisting of caesium ions and magnesium ions, as therapeutically active ingredients, and a carrier for topical administration to a patient, the preparation being a cream, paste, lotion, or spray.

Lines 43-45,

8. A preparation according to Claim 1 wherein the absorbent material is impregnated with caesium chloride and magnesium sulphate.

Column 13,
Lines 1-4, insert the following:

15. A preparation according to Claim 2 wherein the preparation is a cream having a cream base and caesium chloride and magnesium sulphate mixed into the cream base.

UNITED STATES PATENT AND TRADEMARK OFFICE
CERTIFICATE OF CORRECTION

| | |
|---|---|
| PATENT NO. | : 5,945,119 |
| DATED | : August 31, 1999 |
| INVENTOR(S) | : J. Lai |

It is certified that error appears in the above-identified patent and that said Letters Patent is hereby corrected as shown below:

Columns 13 to 14, claim 21,
Lines 23 to 3, insert the following:

21. A pharmaceutical preparation consisting of caesium ions and magnesium ions, as therapeutically active ingredients, and a carrier for internal administration to a patient, the preparation being a solution.

This certificate supersedes Certificate of Correction issued February 5, 2002.

Signed and Sealed this

Ninth Day of April, 2002

*Attest:*

*Attesting Officer*

JAMES E. ROGAN
*Director of the United States Patent and Trademark Office*